US008257281B2

(12) United States Patent
Recker et al.

(10) Patent No.: US 8,257,281 B2
(45) Date of Patent: Sep. 4, 2012

(54) METHOD FOR NORMALIZING THE SPINE

(75) Inventors: David Recker, St. Anthony, IN (US);
Eugene Recker, Jasper, IN (US)

(73) Assignee: Alternative Technologies, LLC, Jasper, IN (US)

( * ) Notice: Subject to any disclaimer, the term of this patent is extended or adjusted under 35 U.S.C. 154(b) by 86 days.

(21) Appl. No.: 12/719,248

(22) Filed: Mar. 8, 2010

(65) Prior Publication Data
US 2010/0154807 A1 Jun. 24, 2010

Related U.S. Application Data

(62) Division of application No. 11/756,965, filed on Jun. 1, 2007, now Pat. No. 7,682,320.

(51) Int. Cl.
*A61B 5/103* (2006.01)
*A61B 5/117* (2006.01)
*G09B 23/28* (2006.01)

(52) U.S. Cl. ........ 600/594; 600/587; 434/262; 434/267; 434/274; 434/275

(58) Field of Classification Search .................. 434/262, 434/267, 274, 275; 600/587, 594
See application file for complete search history.

(56) References Cited

U.S. PATENT DOCUMENTS

| | | | | |
|---|---|---|---|---|
| 3,731,400 | A | * | 5/1973 | Pile et al. ............ 434/272 |
| 4,033,054 | A | | 7/1977 | Fukuoka |
| 4,036,213 | A | * | 7/1977 | Gregory ............ 600/594 |
| 4,624,642 | A | * | 11/1986 | Ferrara ............ 434/274 |
| 4,694,831 | A | | 9/1987 | Seltzer |
| 4,852,553 | A | | 8/1989 | Voykin |
| 5,167,225 | A | | 12/1992 | Cheng-I |
| 5,199,876 | A | | 4/1993 | Waldman |
| 5,417,706 | A | | 5/1995 | Chun |
| 5,551,173 | A | | 9/1996 | Chambers |
| 6,024,575 | A | | 2/2000 | Ulrich |
| 6,132,452 | A | | 10/2000 | Pinter |
| 6,641,599 | B2 | | 11/2003 | Peterson et al. |
| 6,742,289 | B2 | | 6/2004 | Celmo |
| 6,857,139 | B2 | | 2/2005 | Walker |
| 6,921,372 | B2 | | 7/2005 | Shin |
| 7,013,503 | B2 | | 3/2006 | Walker |
| 7,131,952 | B1 | * | 11/2006 | Dickholtz et al. ............ 600/594 |
| 7,167,752 | B2 | | 1/2007 | Lin-Hendel |
| 7,310,564 | B2 | | 12/2007 | Leyerer et al. |
| 7,410,493 | B1 | | 8/2008 | Chen et al. |
| 7,682,320 | B1 | * | 3/2010 | Recker et al. ............ 600/587 |

(Continued)

OTHER PUBLICATIONS

Carter, Mildred, Helping Yourself with Foot Reflexology, West Nyack, 12th printing 1972, pp. 4, 6, 8, 9.

(Continued)

*Primary Examiner* — Sean Dougherty
(74) *Attorney, Agent, or Firm* — Woodard, Emhardt, Moriarty, McNett & Henry LLP

(57) ABSTRACT

Disclosed is a method of normalizing a spine of an individual including identifying a first point on the spine that exhibits the greatest degree of spinal misalignment and the hemisphere of the misalignment. A second point on the back of the individual is identified using a measuring device to measure along the spine a calculated distance specific to the individual. The second point on the back is then translated to the front of the individual opposite the second point to identity a third point. Application of therapeutic treatment near the third point normalizes the spine. In one embodiment, the distance is calculated by dividing the height of the individual by eight.

19 Claims, 11 Drawing Sheets

U.S. PATENT DOCUMENTS

| | | |
|---|---|---|
| 2003/0130696 A1 | 7/2003 | Hurd |
| 2003/0220669 A1 | 11/2003 | Shealy |
| 2004/0000076 A1 | 1/2004 | Celmo |
| 2004/0078885 A1 | 4/2004 | Walker |
| 2005/0114994 A1 | 6/2005 | Walker |
| 2005/0161050 A1 | 7/2005 | Song |
| 2005/0222608 A1 | 10/2005 | Hou et al. |
| 2006/0095087 A1 | 5/2006 | Shin |
| 2007/0078361 A1 | 4/2007 | Wong et al. |
| 2008/0249587 A1 | 10/2008 | Cho et al. |
| 2008/0282580 A1 | 11/2008 | Ji-Woog |

OTHER PUBLICATIONS

Ingham, Eunice D., Stories the Feet Can Tell Thru Reflexology, St. Petersburg, Ingham 8th Printing 1982, pp. 3, 5, 10 and 11.

Byers, Dwight C., Better Health with Foot Reflexology. The Original Ingham Methods, St. Petersburg, FL, Ingham, 1985.

Carter, Mildred, Body Reflexology, Healing at Your Fingertips, Nyack, New York, Parker, 1983, pp. 33, 37-38.

Dougans, Inge, The Complete Illustrated Guide to Reflexology, New York, Barnes & Noble Books 1996, pp. 50-53, 84-85 and 97-99.

Lawrence, d. Baloti and Harrison, Lewis, Massage Works, a Practical Encyclopedia of Massage Techniques, New York, Perigee Books published by the Putnam Publishing Group, 1983, pp. 64-65, 97 and 2 graphs following p. 103.

Dawson, Helen L., Basic Human Anatomy, New York, Appleton-Century-Crafts, 1966, pp. 67-68.

NCAHF Position Paper on Accupuncture (www.ncahf.org/pp/acu.html).

Wikipedia, the free encyclopedia Trigger Point (http://en.wikipedia.org/wiki/Tngger_point).

Wikipedia, the free encyclopedia Referred Pain (http://en.wikipedia.org/wiki/Referred_pain).

\* cited by examiner

METHOD FOR NORMALIZING THE SPINE

This application is a divisional of application Ser. No. 11/756,965, filed Jun. 1, 2007 now U.S. Pat. No. 7,682,320, which is hereby incorporated by reference.

BACKGROUND

Pain management has become a significant struggle in the lives of many people today. Often pain is attempted to be controlled through medication, both through prescription and over the counter forms, with varying degrees of success. Other pain management techniques are also employed, including homeopathic remedies, chiropractic treatments, and acupuncture, to name a few. The efficacy of any type of pain management technique is determined by the skill of the practitioner, whether it be a medical doctor or acupuncturist, for example, and by the receptiveness of the patient to the treatment.

Additionally, most types of pain management or control techniques work by treating the symptoms, or apparent source, of the pain. Massage therapy, for example, is directed to relieving soreness or tightness of particular muscles, and often causes increased discomfort or pain before improvement is felt. What is needed is a process, technique, or device that relieves pain without forcing a patient to feel worse before they feel better. The present disclosure is directed to just such techniques and associated devices.

SUMMARY

The present disclosure is directed to a therapeutic method for normalizing a spine of an individual including identifying a first point on the spine that exhibits the greatest degree of spinal misalignment and the hemisphere of the misalignment. A second point on the back of the individual is found using a measuring device to measure along the spine a calculated distance specific to the individual. The second point on the back is then translated to a third point on the front of the individual opposite the second point. Application of therapeutic treatment near the third point normalizes the spine. In one embodiment, the distance is calculated by dividing the height of the individual by eight.

Further objects, embodiments, forms, benefits, aspects, features and advantages of the present disclosure may be obtained from the description, drawings, and claims provided herein.

DETAILED DESCRIPTION

The present disclosure describes unique pain management or treatment methods, techniques, and devices that operate under the theory that when muscles are relaxed and in balance, the skeletal system of the body will have a tendency to be aligned, and will thus be structurally strengthened. Skeletal alignment improves circulation of the vascular and the nervous systems, increasing energy flow throughout the body, which enhances and allows the body to better heal itself.

Specifically, the present disclosure describes a process that from any specific pain location on the body, a series of specific related points can be found. When these related points are treated, either individually or in some combination, the pain felt at the original complaint point is alleviated or reduced.

Figure 1:
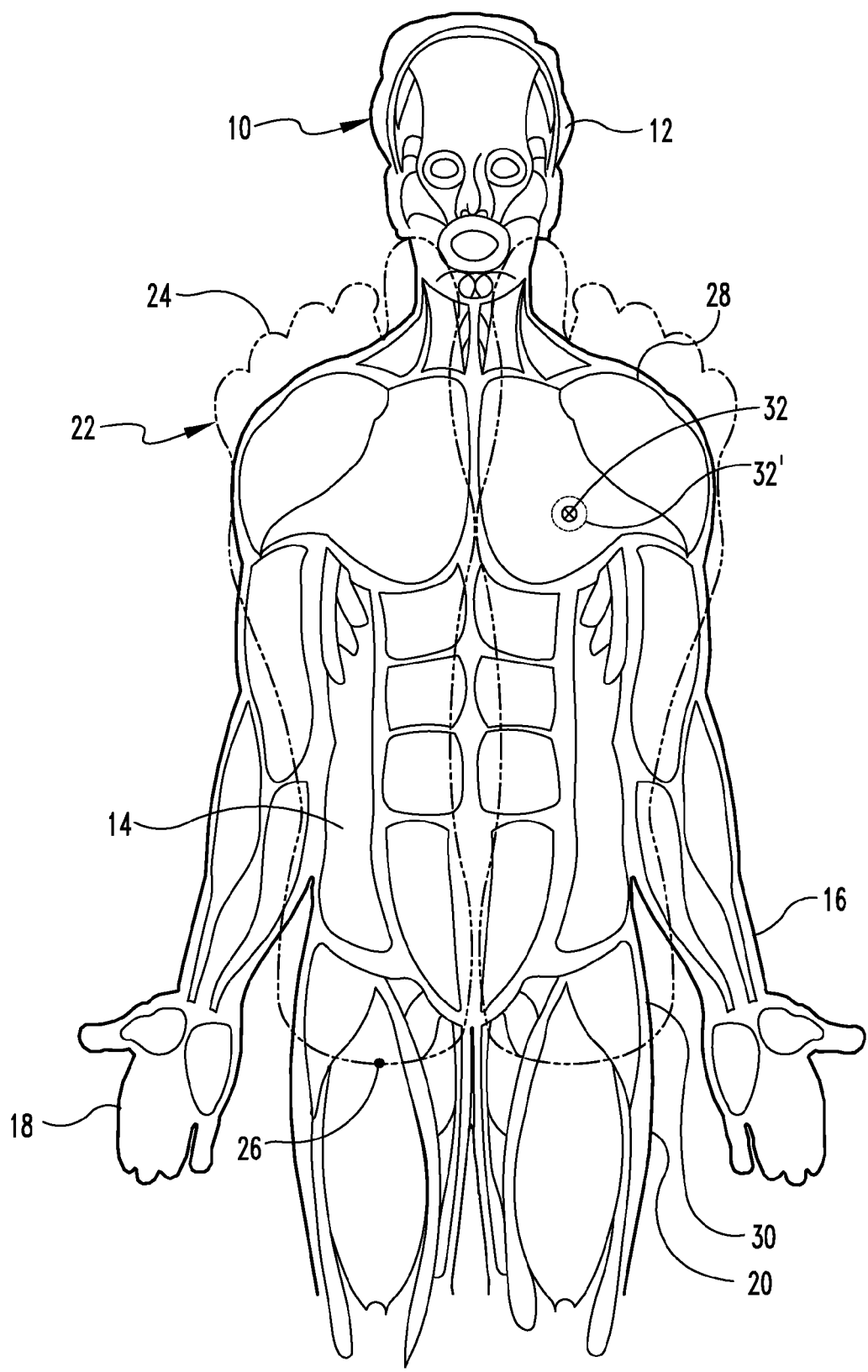
FIG. 1 is a front diagrammatic view of a portion of the human anatomy, illustrating a correlation in accordance with the present disclosure.

In order to describe this process, reference is made to FIG. 1, which shows a drawing 10 illustrating a portion of the typical human anatomy. Drawing 10 shows the head 12, torso 14, arms 16, hands 18, and the upper part of legs 20. Also shown in FIG. 1 is an overlay 22 of a pair of feet. Overlay 22 is scaled to provide a precise correlation between the dimensions of the feet and a particular part of the human anatomy, namely the torso. As can be seen in FIG. 1, overlay 22 extends so as to completely overlay torso 14 thereby providing visible correlations as will be described below. Drawing 10 may be a photograph or outline drawing of an individual patient, and overlay 22 may be a scaled photograph or outline drawing of the actual feet of such patient. Drawing 10 may also be merely a representation of a typical or generic human form, with overlay 22 also being merely a representation of generic human feet. For purposes of explaining the pain treatment method of the present disclosure, the representations are equivalent. In practice, the skill of the therapist or practitioner may determine whether actual or generic patient representations are needed and used. Highly skilled practitioners may not require the creation of a drawing 10 and overlay 22 at all, as they may be able to visualize the feet to torso correlation for a particular patient. Less experienced practitioners or therapists, or those being trained or still learning the methods and techniques of the present disclosure, may find it helpful to create or refer to an actual drawing and overlay in order to understand the principles of the disclosure.

As previously described, overlay 22 is scaled to match the vertical dimensions of torso 14 such that there is a correlation between the torso and the top 24 (toes) and bottom 26 (heel) of the feet, as well as correlations between the feet and the top of the shoulders 28, the fifth metatarsal bone in the foot to the lower rib, the heel 26 to the top of the hip 30, the waistline to the feet, the groin to the heel 26, and the feet to the chest and abdomen. These correlations are formed as part of a locator system that is integral with the present disclosure. The locator system involves, in one component, a series of measurements that are developed for an individual patient to determine the location of the various points on the patient's body that are to be treated. The use of the locator system will be explained in the following paragraphs.

In accordance with one embodiment of the disclosure, an individual (e.g., patient or client) presents themselves to a practitioner of the method of the disclosure with a problem or condition that is causing pain. In some cases the patient may be able to describe the initial event that originally caused the problem, but in other cases the patient may just know that some area of the body hurts or is sore. The practitioner then identifies, through sight or by touch, the spots or areas of tenderness or soreness on the patient's feet. There may be multiple points, spots, or areas of tenderness on the patient's feet. These points or areas of tenderness or soreness, referred to as congested areas, may or may not be related to each other, but typically the most tender spot will relate to that particular pain of which the patient is primarily complaining. The spot or area on the feet that is determined to be the most tender or sore is designated as the primary reference point. In FIG. 1, this is designated as point 32.

As described above, overlay 22 correlates the feet of the patient to torso 14. By this correlation, point 32 on the feet of the patient physically corresponds to a spot or point on torso 14; in FIG. 1, this is illustratively shown as point 32'. This corresponding point 32' is designated as the primary referral point. The patient will typically experience some degree of pain or soreness when the primary referral point is touched. Treating or working the primary referral point 32', e.g., through massage, will relieve at least some, and occasionally all, of the original pain complained of by the patient. The locator system is used to identify additional points or areas of the patient's body which, when treated, will further relieve or alleviate the patient's original pain. These points or spots are designated as related referral points and helper referral points and are located as follows.

With the patient lying down, the therapist or practitioner measures the height or length of the patient from the top of the head to the sole of the feet, i.e., the feet are held perpendicular to the body. This measurement is then divided by four to determine the distance between related referral points, i.e., the distance from the primary referral point to a related referral point and the distance from one related referral point to the next referral point. The distance between related referral points is also divided by two to determine helper referral measurement 67, the distance from a related referral point to a helper referral point. One method of locating referral points is to measure whole number multiples of helper referral measurement 67 away from primary reference point 66. Even whole number multiples, e.g., 2, 4, etc., locate related referral points while odd whole number multiples, e.g., 1, 3, etc., locate helper referral points. The body height or length measurement is recommended to be made with a metric (i.e., base 10) ruler or measuring tape for ease in calculating the related referral point and helper referral point distances. Treating or working each referral point, whether it be a primary referral point, a related referral point, or a helper referral point, will act to reduce or alleviate the pain experienced by the patient. However, merely knowing the distances between referral points is not enough to accurately locate those points on the patient. The additional information that is needed is described as follows.

$$\text{related.referral.measurement} = \frac{\text{height}}{4} \quad (1)$$

$$\text{helper.referral.measurement} = \frac{\text{related.referral.measurement}}{2} = \frac{\text{height}}{8} \quad (2)$$

Referring now to formulas (1) and (2), the calculations for the related referral measurement and the helper referral measurement are expressed as mathematical equations. Referring to formula (2), the helper referral measurement can be calculated by either dividing the related referral measurement by two or by dividing the height of the patient from the top of the head to the sole of the feet by eight.

Figure 10:
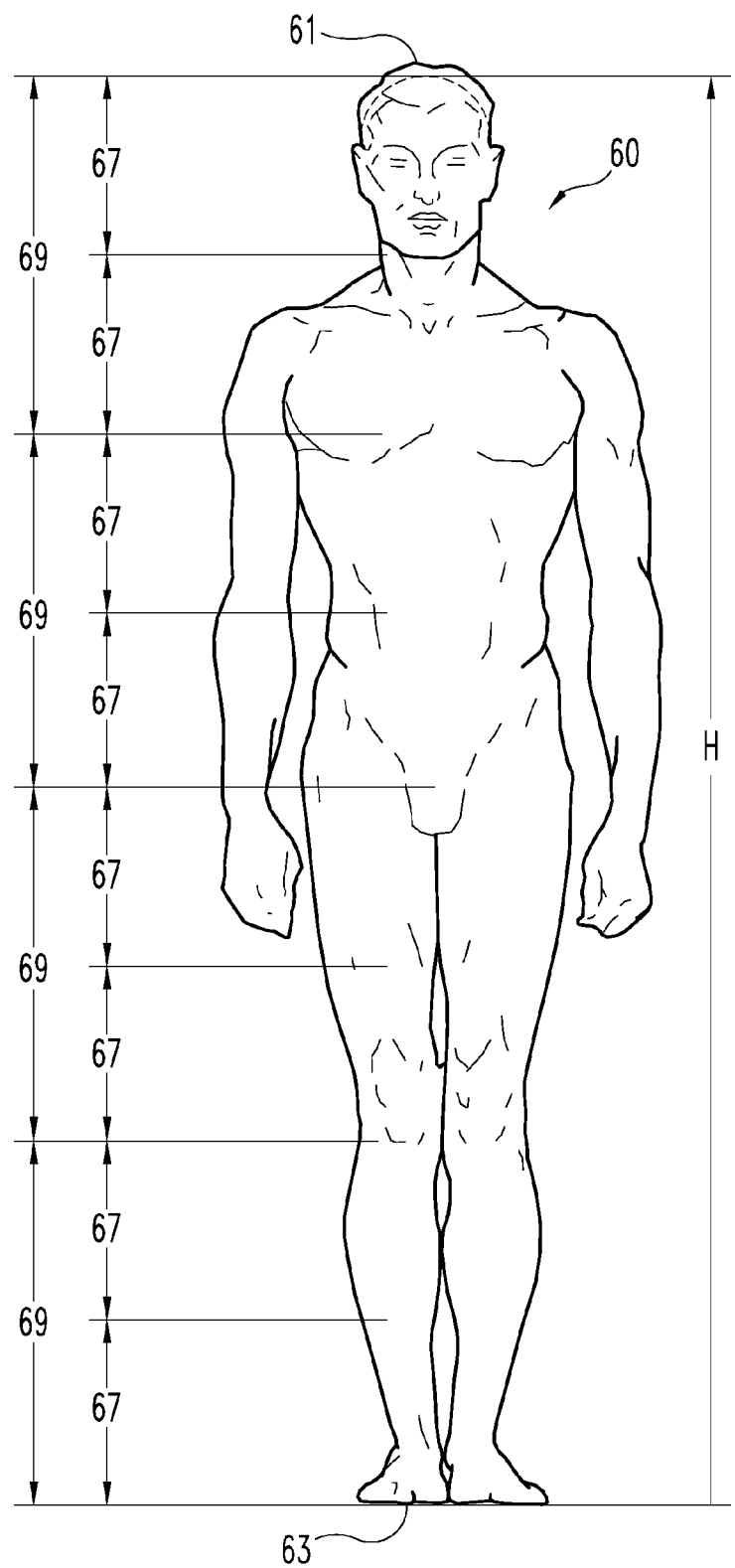
FIG. 10 is a front diagrammatic view of the height measurement of a person between the top of the head and the sole of the feet.

Referring to FIG. 10, the measurements and calculations discussed above are illustrated. FIG. 10 depicts a front view of person 60 including top of the head 61 and sole of the feet 63. Height H is the distance between top of the head 61 and sole of the feet 63. Related referral measurement 69 is determined by dividing height H into four equal lengths, as shown in FIG. 10.

Figure 2:
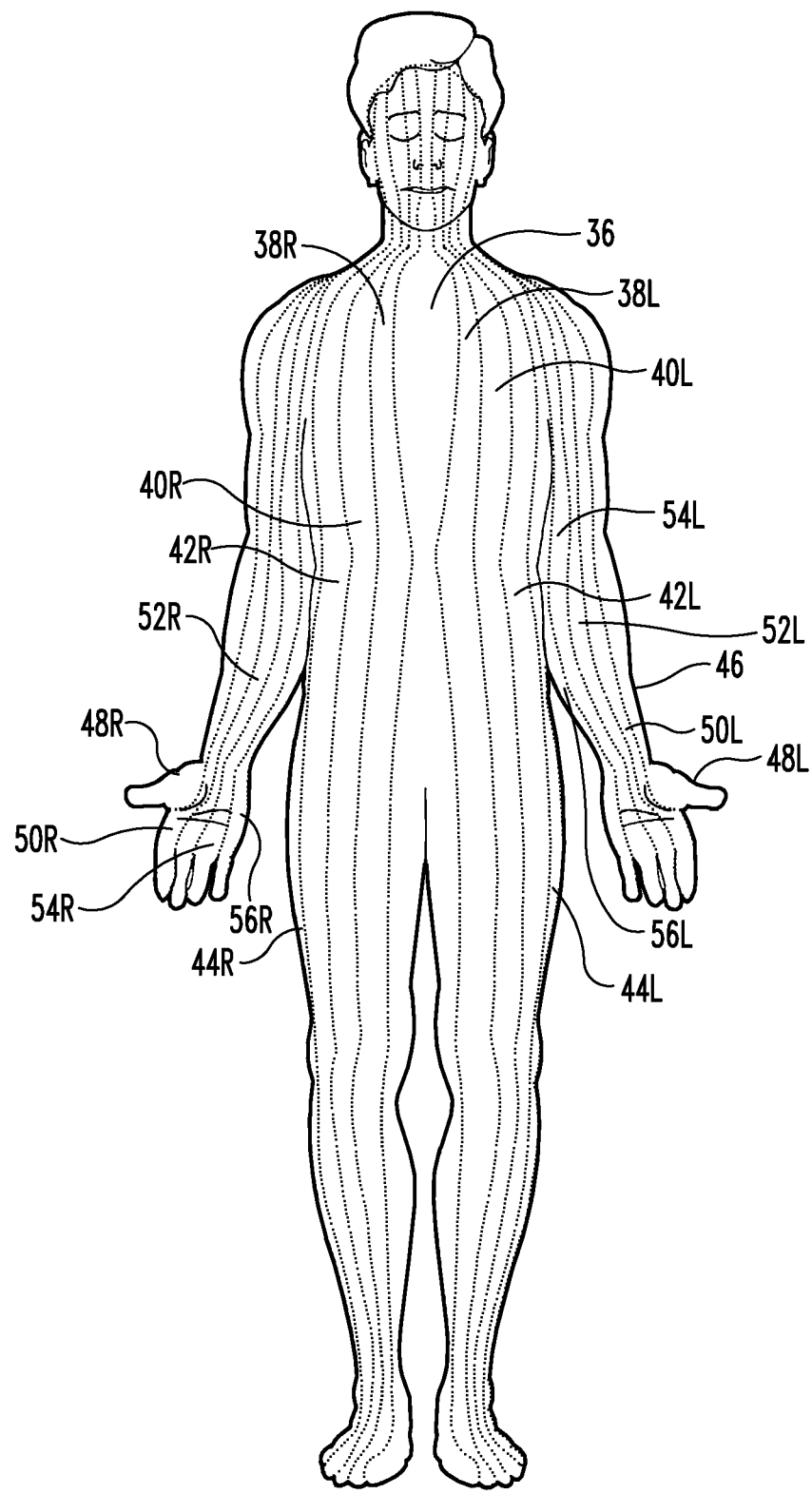
FIG. 2 illustrates a front diagrammatic view of a human form, showing the location of relationship zones in accordance with the present disclosure.
Figure 3A:
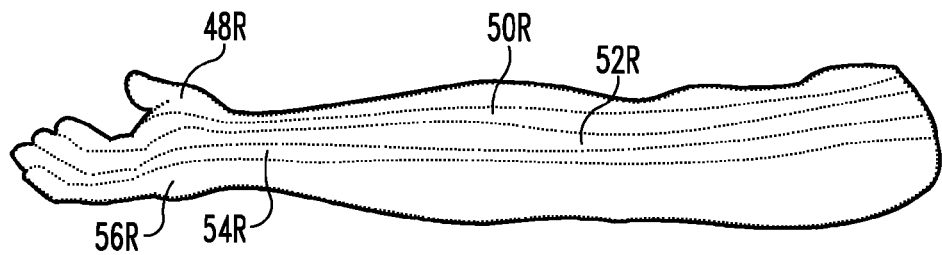
FIGS. 3A, 3B, 3C, and 3D show the location and arrangement of relationship zones in the arm in accordance with the present disclosure, as the arm is held in different positions.
Figure 3B:
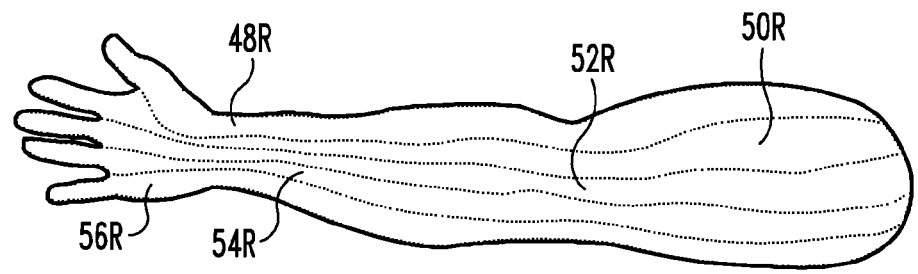
Figure 3C:
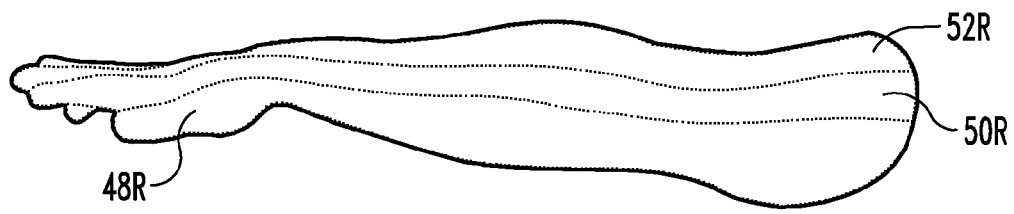
Figure 3D:
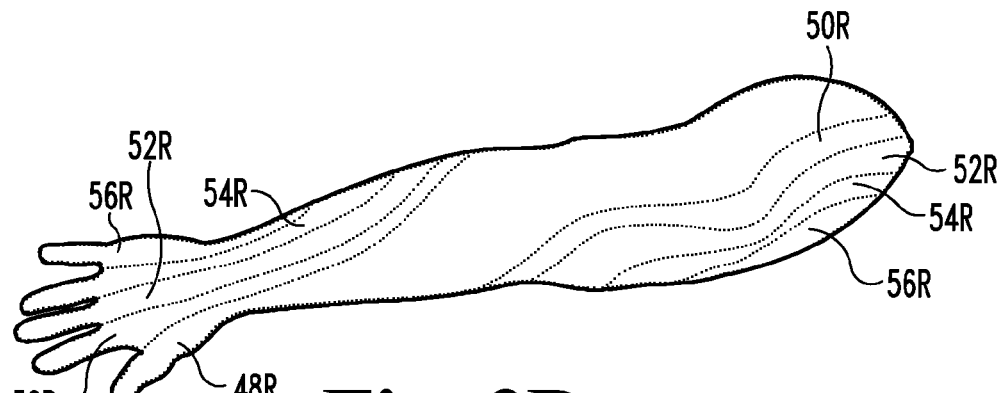

Once the distances between the various referral points are calculated, placement of the actual referral points is made by using the calculated distances and measuring within the particular body zone in which the primary referral point is located. Referring now to FIG. 2, there is shown a human form diagram 34 with body zones identified in accordance with the present disclosure. Diagram 34 comprises a plurality of longitudinal body zones that progress laterally from the median plane. Central zone 36 begins at the top of the head and follows a path through the torso and includes an inner region of each leg and each foot. Symmetrical zones 38L and 38R are located on either side of central zone 36, followed by symmetrical zones 40L and 40R, symmetrical zones 42L and 42R, and symmetrical zones 44L and 44R. The arms 46 of the human form in diagram 34 comprise zones flowing from the head and neck. These zones run diagonally across the vertical zones in the torso and also directly correlate to the respective zones in the rest of the body described above. These zones are identified as zones 48L and 48R, 50L and 50R, 52L and 52R, 54L and 54R, and 56L and 56R. The zones of arms 46 can be seen more clearly in FIGS. 3A and 3B. Each zone defines a particular shape or contour along diagram 34. In accordance with the present disclosure, each related or helper referral point will be located within the same zone as is their primary referral point. With reference to FIGS. 1 and 2, it is apparent that primary referral point 32' is located within zone 40L. Each of the related referral points and helper referral points identified by use of the locator system previously described will therefore also be located within zone 40L. The various zones as illustrated in FIGS. 1-3 are illustratively shown as being well defined with sharp or precise delineations. In practice, however, the crossover between one zone and another may be less sharp, but an experienced practitioner will be able to accurately separate one zone from another through treatment and patient feedback.

Figure 4:
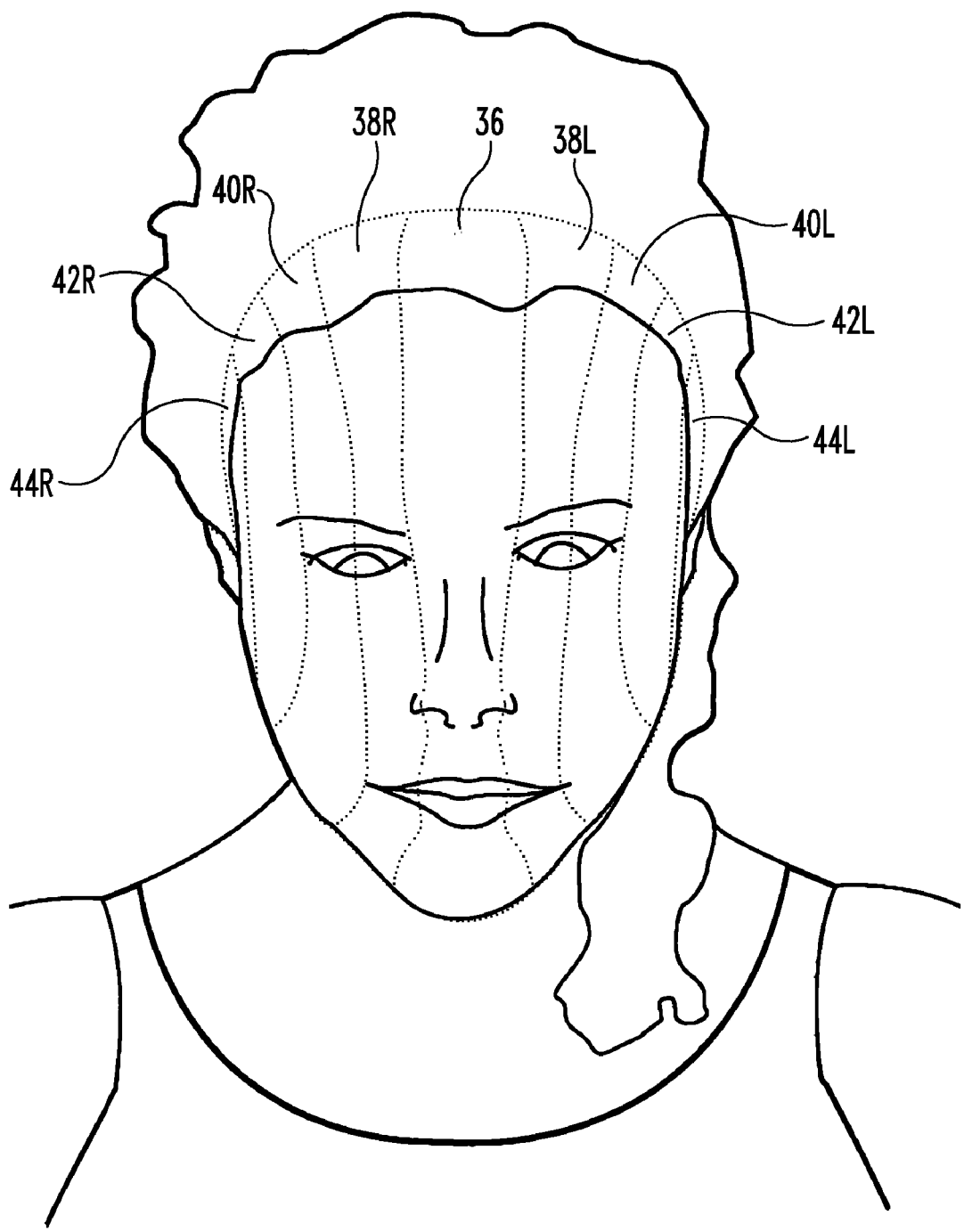
FIG. 4 is a front diagrammatic view of the head, showing the location of relationship zones in accordance with the present disclosure.
Figure 5:
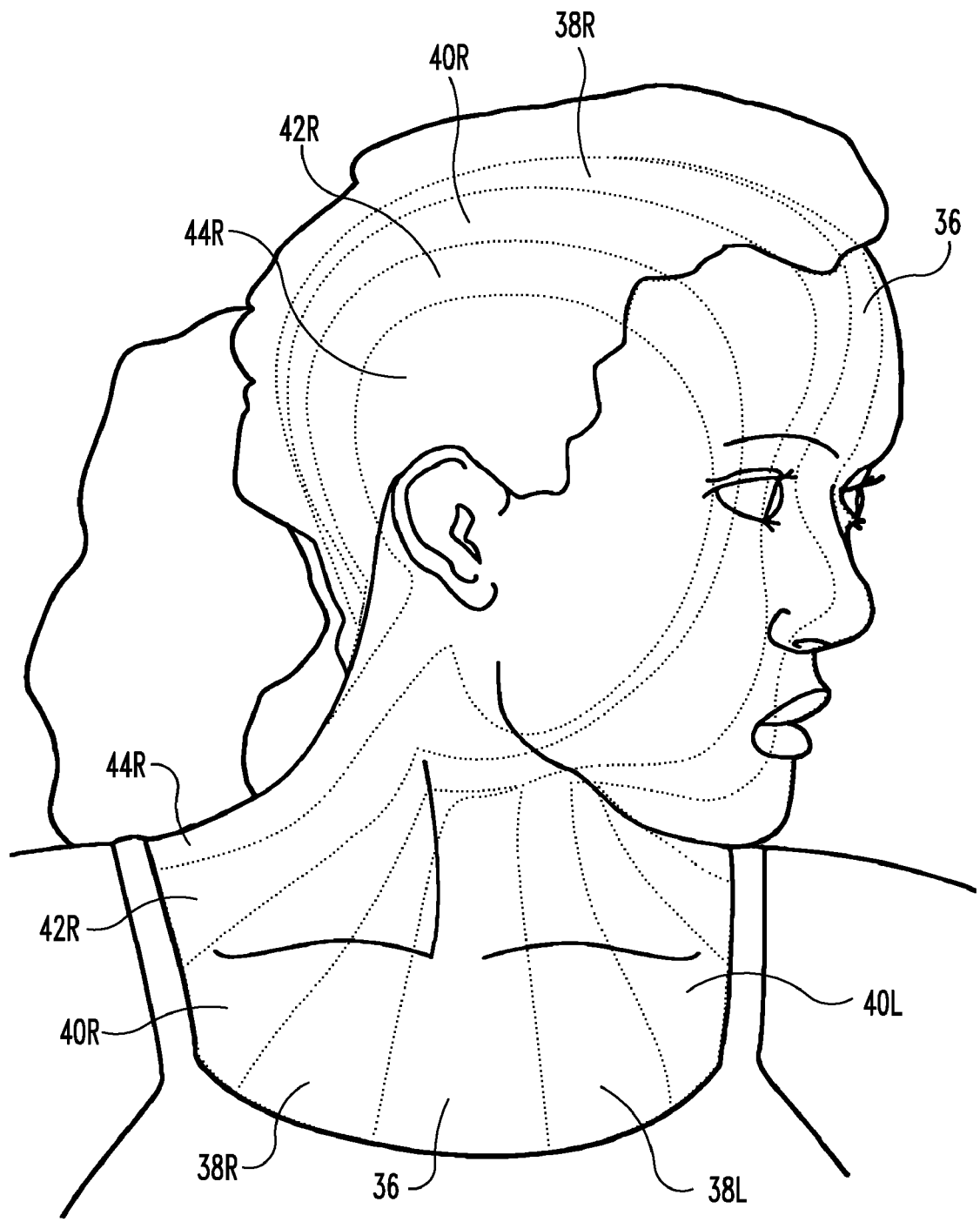
FIG. 5 is a side diagrammatic view of the head, showing the location of relationship zones in accordance with the present disclosure.

FIGS. 4 and 5 illustrate the zones of the head. Although the head zones are continuations of the body zones illustrated in FIG. 2 and consequently are correlated to the body zones, the head zones have particular shapes and define much more specific regions than do the zones that comprise the body, as is particularly apparent in FIG. 5. For that reason, treatment of the head for purposes of pain management requires precision in the locating and defining of the particular zone in which the relevant referral points are to be found.

Figure 6:
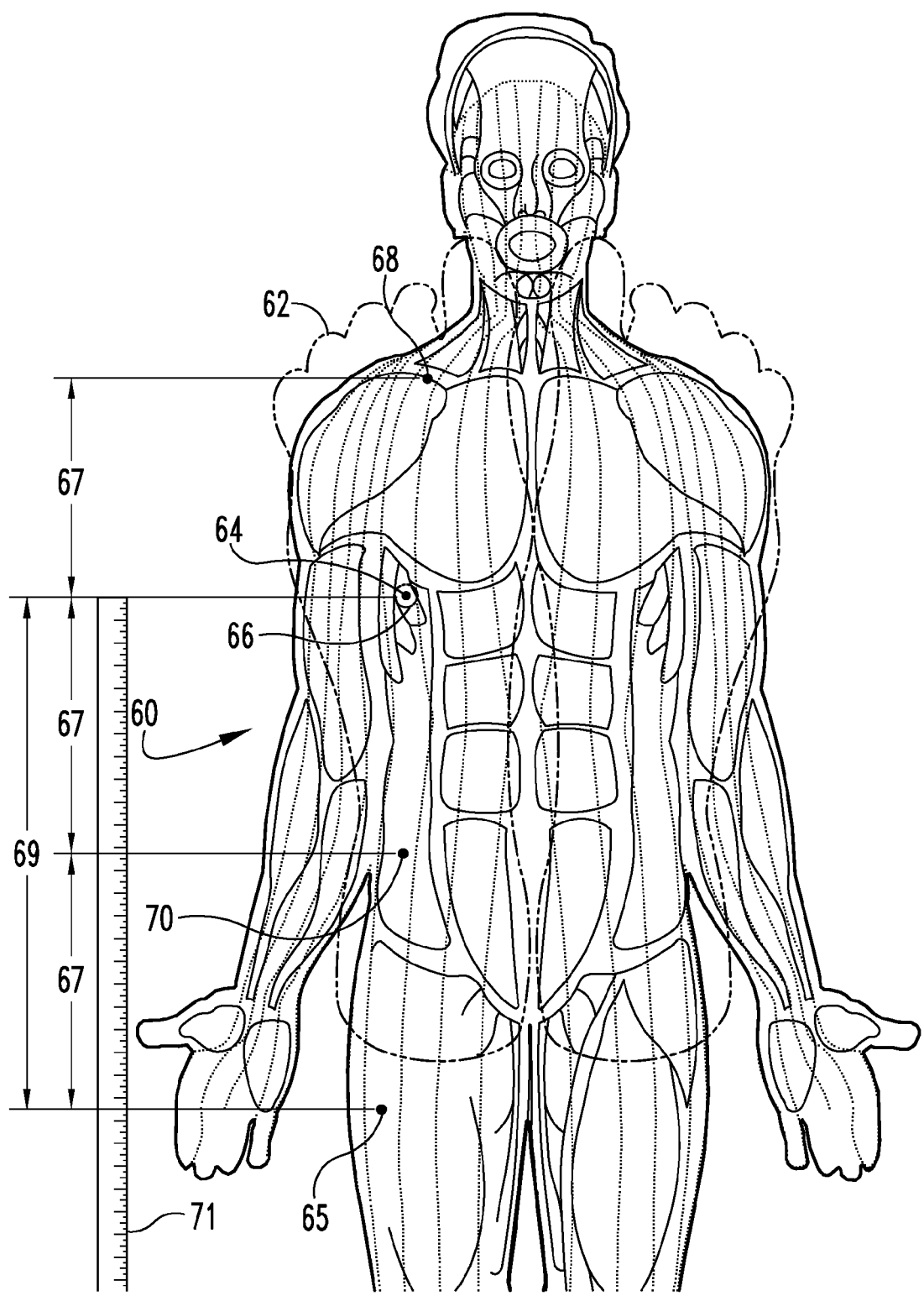
FIG. 6 is a front diagrammatic view of a portion of the human anatomy similar to that shown in FIG. 1, illustrating additional correlations in accordance with the present disclosure.

FIG. 6 illustrates one example of how various referral points can be located on an individual or person 60. The representation of person 60 in FIG. 6 illustrates the previously described zones of the body, head and arms, as well as a scaled overlay 62 of the feet of person 60. As described above, a point of soreness or tenderness in the feet of person 60 defines a primary reference point 64 on overlay 62. This correlates to a primary referral point 66 on the torso of person 60. As can be seen, primary referral point 66 is located within zone 42R. Therefore, all related referral points will also be located within zone 42R. There may, of course, be other areas or points of soreness that define other primary reference points or primary referral points that are located in other zones, but the referral points associated with primary referral point 66 will all be located within zone 42R.

Related referral point 65 is identified and its location determined by measuring one related referral measurement 69 below primary referral point 66 within zone 42R using measuring device 71. (Note that other related referral points can also be located above primary referral point 66, if space permits.) Helper referral points 68 and 70 can be identified and their location determined by measuring one helper referral measurement 67 above and below primary referral point 66 or related referral point 65 within zone 42R using measuring device 71. The locator system can also be used to find additional helper referral points from helper referral points 68 and 70. Treating the various related referral points through massage, manipulation, heat, or other therapeutic means, singly or in combination, will relieve or lessen the soreness associated with primary referral point 66. By treating the helper referral points as well as the primary referral point, pain relief can be realized while avoiding repeated painful treatment or manipulation of only the "sore spot."

The pain management method of the present disclosure therefore can be used to relieve pain without subjecting the patient or client to the added pain of the treatment itself. For this reason, the disclosed pain management method can be used on babies and individuals having low pain tolerance or acute localized pain without aggravating the source of the pain.

Figure 7:
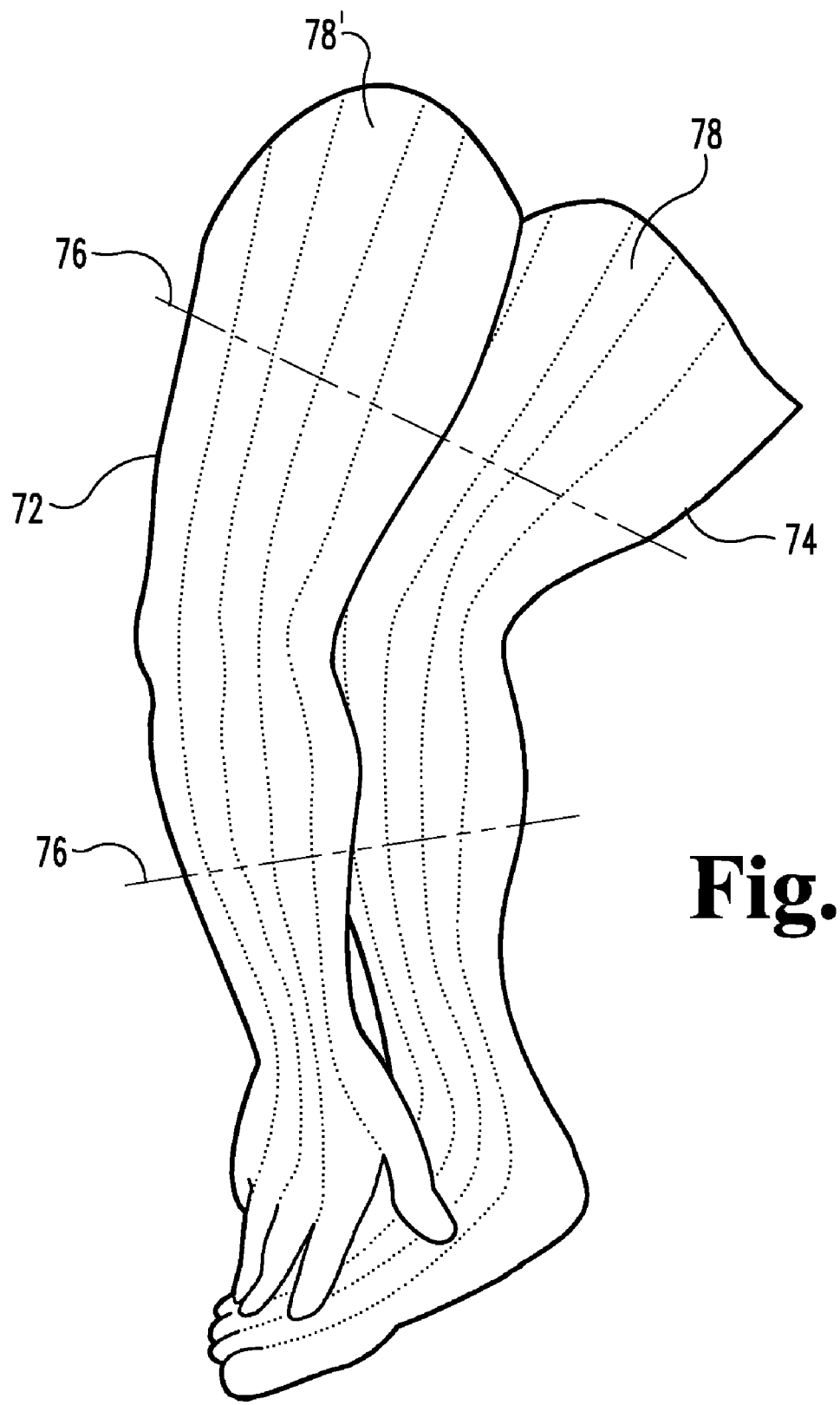
FIG. 7 is a side diagrammatic view illustrating relationship zones in the arm and the leg, and also showing a correlation in accordance with the present disclosure.

Related referral points can be directly correlated from the feet to the torso, from the head or the legs to the torso, or from the torso to the head or legs. Due to a difference in scaling factor, the locator system does not permit direct correlation to and from the arms. However, as shown in FIG. 7, the arm 72 of a patient or client can be physically correlated or scaled to the patient's or client's leg 74, such as along illustrative transfer or correlation lines 76, for example, such that referral points located in the leg can be transferred to the arm, within the corresponding zone (e.g., zones 78 and 78'), for treatment, or points of soreness in the arm can be transferred to the leg where the locator system will then allow direct correlation to the primary referral point 66 on the torso, and subsequently, other body parts to locate the related referral points such that treatment of such referral points will act to alleviate the pain or soreness in the arm.

Figure 8:
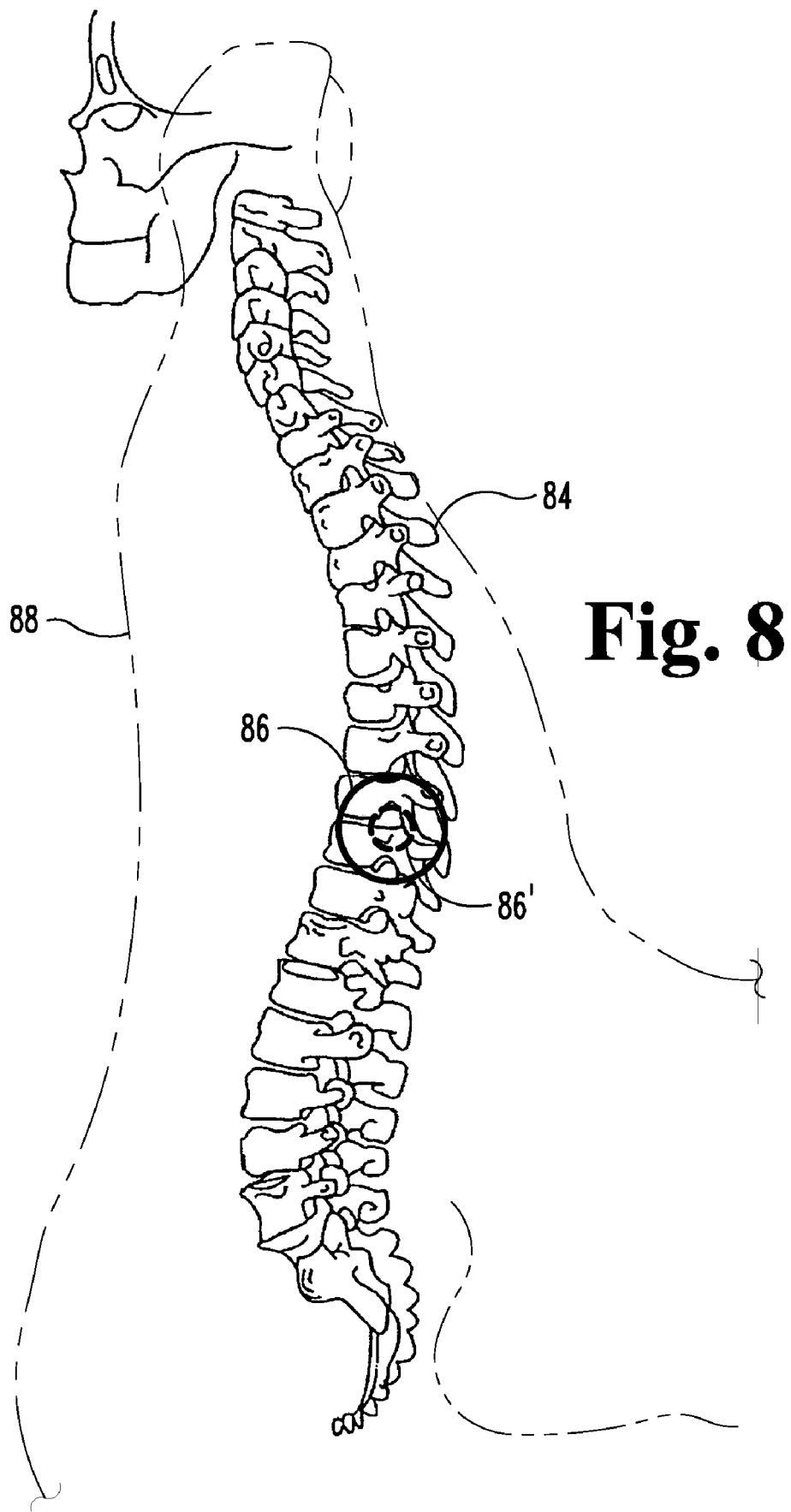
FIG. 8 is a side diagrammatic view of another portion of the human anatomy, illustrating another correlation in accordance with the present disclosure.

The previous description has explained the correlation between tenderness or soreness along the bottom of a patient's feet with a source of pain or discomfort in other regions of the body. Human form diagram 34, depicted in FIG. 2, illustrates that the spine and the inside of the feet are all in zone 36 and that the left foot is in the left hemisphere and the right foot is in the right hemisphere. FIG. 8 illustrate a correlation of the spine to the feet. An area of discomfort, or "sore spot," along the inside of the feet can be correlated to skeletal pain in the spine or back. FIG. 8 depict an overlay of foot 88 superimposed on spine 84. From the depicted overlay, it is possible to translate pain in the inside of foot 88 to a specific area or location along spine 84 that is causing the associated body or skeletal pain. For example, as depicted in FIG. 8, sore spot 86 along the inside of foot 88 correlates to a primary referral point 86' on spine 84. Using the locator system described above with respect to primary referral point 86' on spine 84 will lead to the identification of related and helper referral points that, when treated, will aid in the overall reduction of pain and discomfort felt by the patient.

Figure 9A:
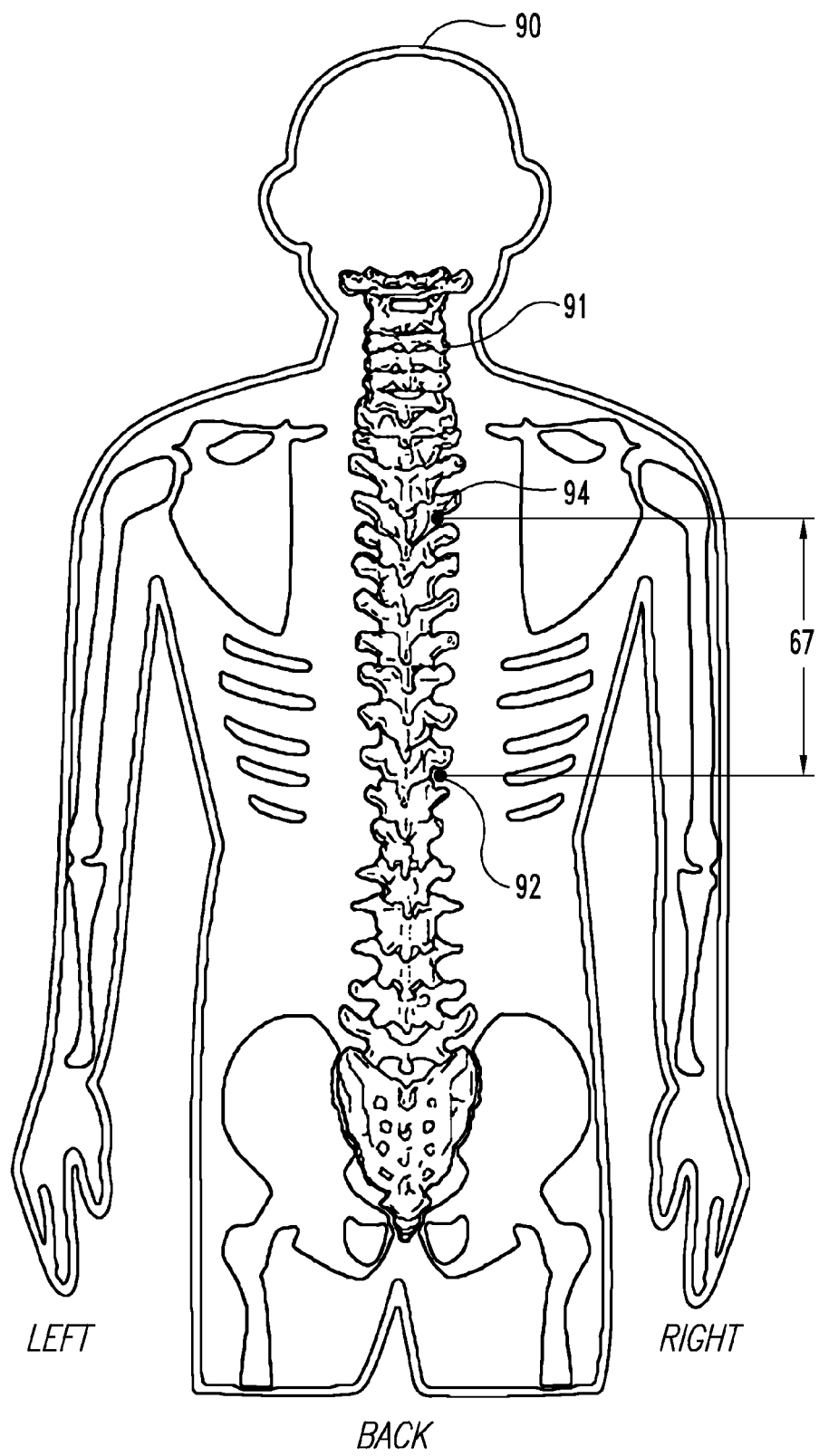
FIG. 9A is a back diagrammatic view illustrating a portion of the typical human anatomy including the spine, illustrating a correlation in accordance with the present disclosure.
Figure 9B:
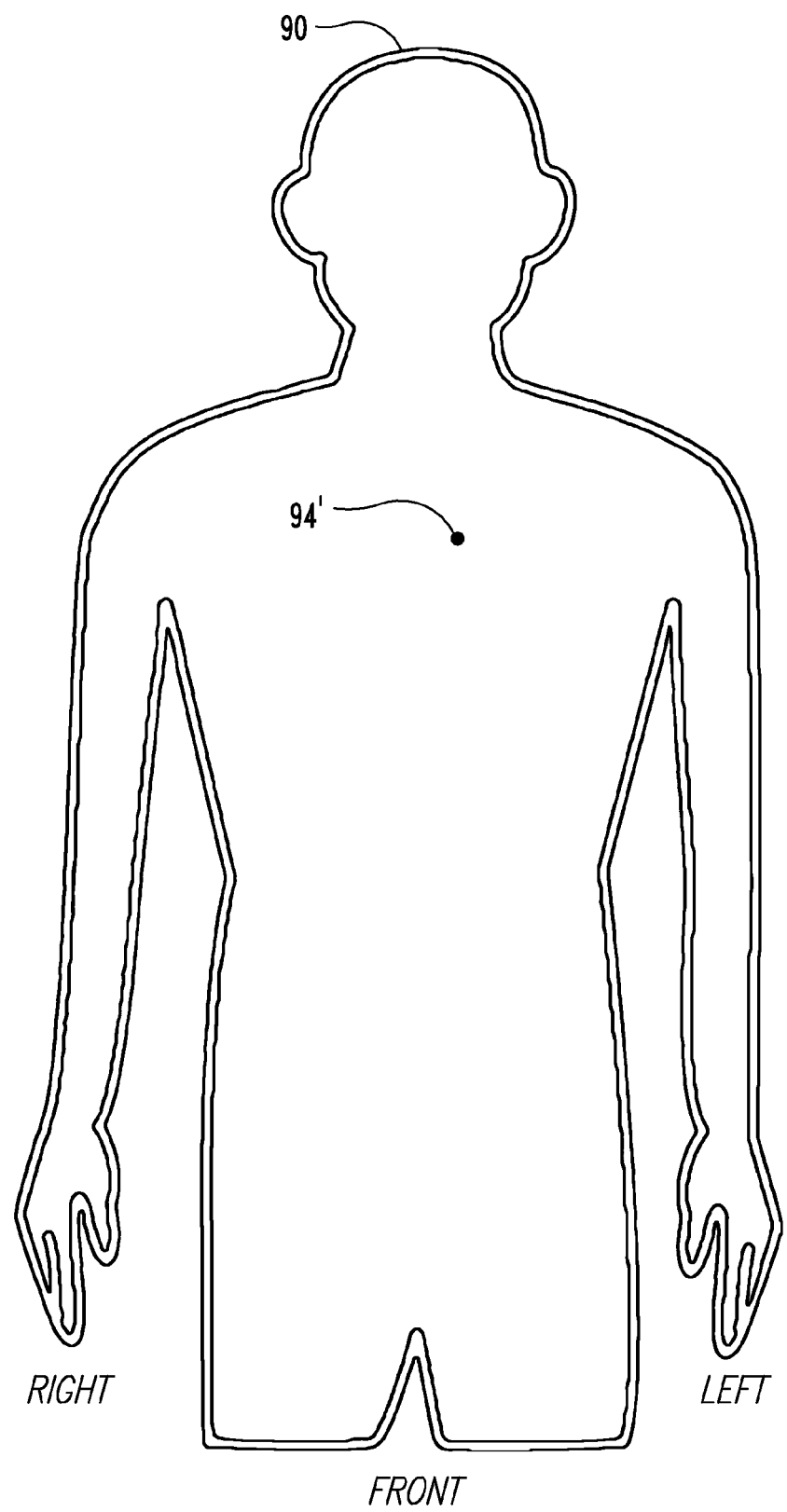
FIG. 9B is a front diagrammatic view illustrating a view of a human torso, illustrating a correlation in accordance with FIG. 9A.

Another embodiment of the disclosure is depicted in FIGS. 9A and 9B which show drawing 90 illustrating a portion of the typical human anatomy including spine 91 illustrated in FIG. 9A. This embodiment deals with normalizing the spine using the same overall techniques described above. With the patient lying on their stomach, the therapist or practitioner observes the spine to find the point at which the spine is exhibiting the greatest degree of misalignment, which is illustrated as point 92 in FIG. 9A. The therapist or practitioner also notes whether the spine at point 92 is being pulled to the right or left hemisphere of the torso.

The therapist or practitioner then measures up (or down) one helper referral measurement 67 from point 92 to point 94 in zone 36 and either physically or mentally marks point 94 on the back. The actual treatment area 94' is on the front of the torso, directly opposite point 94, as illustrated in FIG. 9B.

The therapist or practitioner then works treatment area 94' on the front of the torso. The therapist or practitioner interacts with the patient to verify the exact location by degree of tenderness or soreness and then works that area until the tenderness/soreness subsides. Zone 36 (the zone the spine is in) extends to both the left and right hemispheres of the body. The therapist or practitioner works in the same hemisphere of the body that the spine is pulled towards at point 92. By relaxing the tight muscles that are pulling the spine to either the right or left hemispheres of the torso, the spine is allowed to normalize by reverting to its normal, straight, position.

The therapist or practitioner then rechecks the alignment of the spine with the patient lying on their stomach. For some patients, the spine will normalize itself very easily. In other patients, it may take several iterations of the process described above to fully normalize the spine. After each iteration, the therapist or practitioner rechecks the spine for the point of greatest misalignment. If a new point of misalignment is discovered, this creates a new treatment point 92 and thus, a different treatment area 94' as detailed above.

Spine normalization, as described herein, when used in conjunction with the other embodiments described herein, may provide an overall reduction of pain related to other treatments and for some patients, spine normalization increases how long the benefits of other treatments last. Thus, it is preferable to use spine normalization as the first treatment applied to a patient.

While the disclosure has been illustrated and described in detail in the drawings and foregoing description, the same is to be considered as illustrative and not restrictive in character, it being understood that only the preferred embodiments have been shown and described and that all changes, modifications and equivalents that come within the spirit of the disclosure provided herein are desired to be protected. The articles "a", "an", "said" and "the" are not limited to a singular element, and may include one or more such elements.

What is claimed is:

1. A method of normalizing the spine of an individual, the individual having a height from a top of the head to soles of the feet, a front and a back the method comprising:

identifying a first point on the spine where the spine exhibits a greatest degree of spinal misalignment;

identifying a hemisphere of misalignment at the first point;

calculating a distance by dividing the height of the individual from the top of the head to the soles of the feet by eight;

using a ruler, measuring along the spine on the back approximately the distance away from the first point to locate a second point on the back;

translating the second point on the back of the individual to a third point on the front of the individual;

locating a treatment area proximate to the third point and in the hemisphere of misalignment;

applying a therapeutic treatment to the treatment area to normalize the spine.

2. The method of claim 1, further comprising identifying the first point on the spine by observing the spine of the individual and identifying where the spine is exhibiting the greatest degree of misalignment.

3. The method of claim 2, wherein the first point on the spine is identified when the individual is lying face down.

4. The method of claim 1, further comprising identifying the hemisphere of misalignment at the first point by observing a direction the spine is misaligned at the first point.

5. The method of claim 2, further comprising identifying the hemisphere of misalignment at the first point by observing the direction the spine is misaligned at the first point.

6. The method of claim 1, wherein the third point on the front of the individual is directly opposite the second point on the back of the individual.

7. The method of claim 2, wherein the third point on the front of the individual is directly opposite the second point on the back of the individual.

8. The method of claim 1, further comprising identifying the first point on the spine by observing the spine of the individual and identifying where the spine is exhibiting the greatest degree of misalignment.

9. The method of claim 8, wherein the first point on the spine is identified when the individual is lying face down.

10. The method of claim 1, further comprising identifying the hemisphere of misalignment at the first point by observing a direction the spine is misaligned at the first point.

11. The method of claim 1, wherein the third point on the front of the individual is directly opposite the second point on the back of the individual.

12. The method of claim 1, wherein the treatment area exhibits soreness and the therapeutic treatment to the treatment area reduces the soreness.

13. A method of normalizing the spine of an individual, the individual having a height from a top of the head to soles of the feet, a front and a back, the method comprising:

identifying a first point on the spine where the spine exhibits a greatest degree of spinal misalignment;

identifying a hemisphere of misalignment at the first point;

calculating a distance by dividing the height of the individual from the top of the head to the soles of the feet by eight;

using a ruler, measuring along the spine on the back approximately the distance away from the first point to locate a second point on the back;

translating the second point on the back of the individual to a third point on the front of the individual;

locating a treatment area proximate to the third point and in the hemisphere of misalignment, wherein the treatment area exhibits soreness;

manipulating the treatment area to reduce the soreness and to normalize the spine.

14. The method of claim 13, further comprising interacting with the individual to confirm the location of the treatment area by evaluating a degree of soreness at the third point.

15. The method of claim 14, further comprising manipulating the treatment area until the soreness subsides.

16. The method of claim 15, wherein the third point on the front of the individual is directly opposite the second point on the back of the individual.

17. The method of claim 13, further comprising identifying the first point on the spine by observing the spine of the individual and identifying where the spine is exhibiting the greatest degree of misalignment.

18. The method of claim 17, wherein the first point on the spine is identified when the individual is lying face down.

19. The method of claim 13, wherein the third point on the front of the individual is directly opposite the second point on the back of the individual.

* * * * *